US010702222B2

(12) United States Patent
Gao et al.

(10) Patent No.: US 10,702,222 B2
(45) Date of Patent: Jul. 7, 2020

(54) CAGE-TYPE CT SCANNER

(71) Applicant: Suzhou Institute of Biomedical Engineering and Technology Chinese Academy of Sciences, Suzhou, Jiangsu (CN)

(72) Inventors: Xin Gao, Suzhou (CN); Zhi yuan Liang, Suzhou (CN)

(*) Notice: Subject to any disclaimer, the term of this patent is extended or adjusted under 35 U.S.C. 154(b) by 0 days.

(21) Appl. No.: 16/344,591

(22) PCT Filed: Dec. 21, 2017

(86) PCT No.: PCT/CN2017/117793
§ 371 (c)(1),
(2) Date: Apr. 24, 2019

(87) PCT Pub. No.: WO2018/121410
PCT Pub. Date: Jul. 5, 2018

(65) Prior Publication Data
US 2019/0239827 A1      Aug. 8, 2019

(30) Foreign Application Priority Data

Dec. 26, 2016   (CN) .......................... 2016 1 1271461

(51) Int. Cl.
*A61B 6/03*      (2006.01)
*A61B 6/00*      (2006.01)
(52) U.S. Cl.
CPC ............ *A61B 6/035* (2013.01); *A61B 6/4064* (2013.01); *A61B 6/4208* (2013.01); *A61B 6/4405* (2013.01); *A61B 6/4429* (2013.01); *A61B 6/4435* (2013.01); *A61B 6/4085* (2013.01)

(58) Field of Classification Search
CPC ..... A61B 6/035; A61B 6/4064; A61B 6/4085; A61B 6/4208; A61B 6/4405; A61B 6/4429; A61B 6/4435
See application file for complete search history.

(56) References Cited

U.S. PATENT DOCUMENTS

2014/0016758 A1* 1/2014 Theiss .................... A61B 6/035
378/197

FOREIGN PATENT DOCUMENTS

CN         105232076 A  *  1/2016

* cited by examiner

*Primary Examiner* — David P Porta
*Assistant Examiner* — Fani Boosalis
(74) *Attorney, Agent, or Firm* — Renner Kenner Law Firm

(57) ABSTRACT

The present invention discloses a cage-type CT scanner. The present invention involves reducing the rotation arc of the rotating member and the vibration amplitude of the whole machine by means of reducing the volume and weight of the CT scanner, without reducing the vibration of the CT scanner itself by eliminating eccentric force in transmission via balance correction or by any other means. Moreover, in the present invention, no crawler that realizes mechanical driving is used so as to decrease the parts in the motor's synchronization structure. Such efforts help reduce costs and allow the CT scanner to be suitable for more applications.

8 Claims, 4 Drawing Sheets

CAGE-TYPE CT SCANNER

FIELD OF THE INVENTION

The present invention relates to medical apparatus, and more particularly to a cage-type CT scanner.

STATE OF THE ART

Cone beam CT systems have developed rapidly since it was available for clinical purposes at the beginning of this century. Mobile medical equipment for field operations will serve as an important medical apparatus for the injured in future hi-tech warfare and play a critical part in major disaster relief. However, field operations involve hostile environments where large traditional CT scanners fail to provide appropriate bedside scanning for critical patients.

Although small CT products are available, they all involve technologies similar to traditional CT, such as scintillator detector arrays, slip ring based data transmission and helical scanning. Moreover, they are only capable of tomographic reconstruction: the X-ray source and the detector are installed on the turntable, and when the turntable rotates, the detector receives X-rays that pass through human organs or tissues; then computer software is used for 3D image reconstruction based on data acquired. To ensure further convenience and adaptability to the future market, it is necessary to accordingly expand diagnosis functions of bedside CT scanners, such as digital radiography (DR) and X-ray scanning, and allow doctors to choose a reasonable examination means based on patients' body parts examined, examination expenses and image resolution.

In addition, mobile scanners are supposed to be optimized. Taking the patent No. 201510627371 as an example, it involves reducing the rotation arc of the rotating member and the vibration amplitude of the whole machine by means of reducing the volume and weight of the CT scanner. For that patent, the design of the drag chain is an original work by the research team, but brings about a challenge—dynamic balance, which means it is necessary to reduce the vibration of the CT scanner itself by eliminating eccentric force in transmission via balance correction or by any other means, with an aim to reduce the requirements on the floor on which the CT scanner works.

Bedside CT scanners are light and small and move flexibly; however, those available in the market are all provided with a large ring structure which serves as the rotating member. The engine, fixed to the rack, drives the large ring to rotate through transmission and connection among mechanical parts, but the mechanical efficiency of the engine is often impaired because the turntable is heavily loaded by the X-ray source and the detector. Hence, mobile field hospitals need more power. Taking as an example the small CT scanner which is designed by Neurologica, an American company, and equipped with a crawler for the purpose of synchronous driving, such CT scanner has a stable center of gravity but cannot work on ordinary floors or in the field; in addition, due to common problems in transmission by belts plus wheels, including belt slippage and locking, it is not suitable for high-accuracy field rescues.

DESCRIPTION OF THE INVENTION

As a minimum, it is an object of the present invention to solve the problems mentioned above and provide the advantages as follows.

The present invention mainly addresses the technical problem that the floors on which CT scanners work are demanding. The present invention involves reducing the rotation arc of the rotating member and the vibration amplitude of the whole machine by means of reducing the volume and weight of the CT scanner, without reducing the vibration of the CT scanner itself by eliminating eccentric force in transmission via balance correction or by any other means. Moreover, in the present invention, no crawler that realizes mechanical driving is used so as to decrease the parts in the motor's synchronization structure. Such efforts help reduce costs and allow the CT scanner to be suitable for more applications.

To achieve these objects and other advantages in accordance with the present invention, the present invention provides a cage-type CT scanner, including:

A rack, vertically arranged on the mobile unit of the CT scanner; a cage-type rotating member, including a first rotating accessory, a second rotating accessory, and a ridge that connects the first rotating accessory and the second rotating accessory; the first rotating accessory is so arranged on the rack through the slewing bearing in a rotatable manner; the cage-type rotating member and the rack form a ring structure whose center serves as the scanning hole; an imaging system, equipped with the X-ray source assembly and the detector assembly that are arranged on the walls at the same side of the second rotating accessory, symmetrically along the shaft center; the X-ray source assembly and the detector assembly are fixed at the second rotating accessory; the detector assembly receives the emergent rays from the X-ray source assembly; and a turbine assembly, arranged on the first rotating accessory in a slanting direction; the gearwheel engaged with the turbine assembly is fixed on the side of the rack that is not the side where the first rotating accessory is; the first rotating accessory, rack, gearwheel and second rotating accessory have coincident axes; the turbine assembly, with the help of the motor, drives the cage-type rotating member to rotate around the gearwheel; the cable, through the cage-type rotating member, connects the power source and the imaging system. The X-ray source assembly emits cone beams, and the imaging system scans and images the object by completing dynamic volumetric scanning in one revolution.

Preferably, the outer ring of the slewing bearing is installed on the inner ring of the rack; the first rotating accessory has an outer ring that is smaller than the inner ring of the rack, and is subject to clearance fit with the rack by means of the slewing bearing; a ball or roller is installed between the wall on the side where the outer ring of the first rotating accessory protrudes and the rack, and on the outer wall of the inner ring of the rack, a groove is arranged to house the ball or roller; the radius of the rack is between the gearwheel and the first rotating accessory, and the gearwheel is a helical gear bolted on the rack.

Preferably, the turbine assembly includes: a turbine shaft, arranged on the cage-type rotating member by means of a base plate; the base plate is fixed on the ridge of the cage-type rotating member by means of a structural section; the turbine shaft is supported by the base plate with roller bearings on both sides; a worm, connected with the turbine shaft by means of an internal spline; the turbine is connected with the engine by means of the brake device on one end and is provided with a belleville spring and gland on the other end; when applied with an axial force generated when the worm and the gearwheel are engaged to transfer force, the turbine shaft directly drives the cage-type rotating member to rotate around the shaft clockwise or counterclockwise depending on the motor rotation; a brake switch, equipped with a groove on one end; the groove is fitted with the protruding part of the initial bar, and on the other end, fixed on the base plate and close to the engine; when the motor does not work, the protruding part of the initial bar will be stuck in the groove of the brake switch, that is to say, the brake switch is at the initial position.

Preferably, an industrial personal computer A is installed on the cage-type rotating member and under the detector assembly, and is equipped with a power source and a command processor. The detector assembly includes an image pre-processing device which processes a first image signal. The first image signal has an imaging portion that shows the photographed object and a margin portion around the imaging portion. The image pre-processing device includes: a margin detecting member that detects the margin portion of the first image signal; a concerned area setting member that sets an initial concerned area corresponding to the imaging portion of the first image signal based on the margin portion detected by the margin detecting member; and a concerned area image generation member that generates a concerned area image signal which indicates the initial concerned area set by the concerned area setting member.

Preferably, the concerned area image generation member includes: a cutting member that cuts from the first image signal the initial concerned area set by the concerned area setting member; and a zooming member that generates an image as the concerned area image signal after it zooms in or out on the displayed object corresponding to the first image signal and after the cutting member cuts the initial concerned area from the first image signal.

Preferably, the cage-type rotating member is equipped with a display that includes an industrial personal computer B, an AC-DC power source and a graphic display. The industrial personal computer B is installed on the ridge at one side of the rotating member while the graphic display is installed in a movable manner on the ridge at the other side of the rotating member, and may be observed from different positions. The industrial personal computer B is powered by the AC-DC power source. The display shows images output by the image processing device.

Preferably, a wireless data communication module is provided on the cage-type rotating member, including: a first memory, so constructed as to store clinical data; a transmitter, so constructed as to transmit the clinical data based on a first communication protocol; a receiver, so constructed as to receive augmented data based on a second communication protocol; and a second memory, so constructed as to store the augmented data. The augmented data are based on the clinical data.

Preferably, an emergency stop button switch and a ray indicator light are installed on the mobile unit.

Preferably, an isolation transformer and an image processing computer are arranged under the mobile unit; the storage medium connected with the image processing computer is installed on the panel. The image processing computer pre-produces a 3D CT image reconstruction algorithm.

Preferably, the power supply is realized by a slip ring.

The present invention has the following benefits at least:

1. The CT scanner is easy to manufacturer and install because all imaging devices are integrated on the cage-type rotating member that includes a first rotating accessory, a second rotating accessory and a ridge that connects the first rotating accessory and the second rotating accessory, and is much lighter and smaller than the patent No. 201510627371 described in the State of the Art because belts and wheels are eliminated;

2. The CT scanner may reduce the workload of operators before images indicating concerned areas are obtained from image signals that are input, because it includes: a margin detecting member that detects the margin portion of the first image signal; the first image signal has an imaging portion that shows the photographed object and a margin portion around the imaging portion; a concerned area setting member that sets an initial concerned area corresponding to the imaging portion of the first image signal based on the margin portion detected by the margin detecting member; and a concerned area image generation member that generates a concerned area image signal indicating the initial concerned area set by the concerned area setting member and automatically generates images of concerned areas corresponding to the imaging portion;

3. The CT scanner requires less cables, greatly reduces their winding, dragging and loosening, and allows for convenient data transmission and backup, because it includes a wireless data communication module that includes a first memory so constructed as to store clinical data, a transmitter so constructed as to transmit the clinical data based on a first communication protocol, a receiver so constructed as to receive augmented data based on a second communication protocol, and a second memory so constructed as to store the augmented data.

4. The present invention provides a mobile CT scanner that realizes tomography and fluoroscopy and may be used in emergency rooms, ICUs and general wards and mounted on vehicles, ships and planes to help with first aid for critical illness and field injuries by scanning the patients who have access to monitoring and rescue equipment.

Additional advantages, objects and features of the present invention will be set forth in part in the description which follows and in part will become apparent to those skilled in the art upon examination of the following or may be learned from practice of the present invention.

DETAILED DESCRIPTION OF THE EMBODIMENTS

The following is devoted to further description of the present invention in conjunction with the accompanying drawings to enable embodiments by those skilled in the art.

It shall be understood that the terms like "include" and "comprise" do not exclude the presence or addition of one or more additional members or their combinations.

Figure 1:
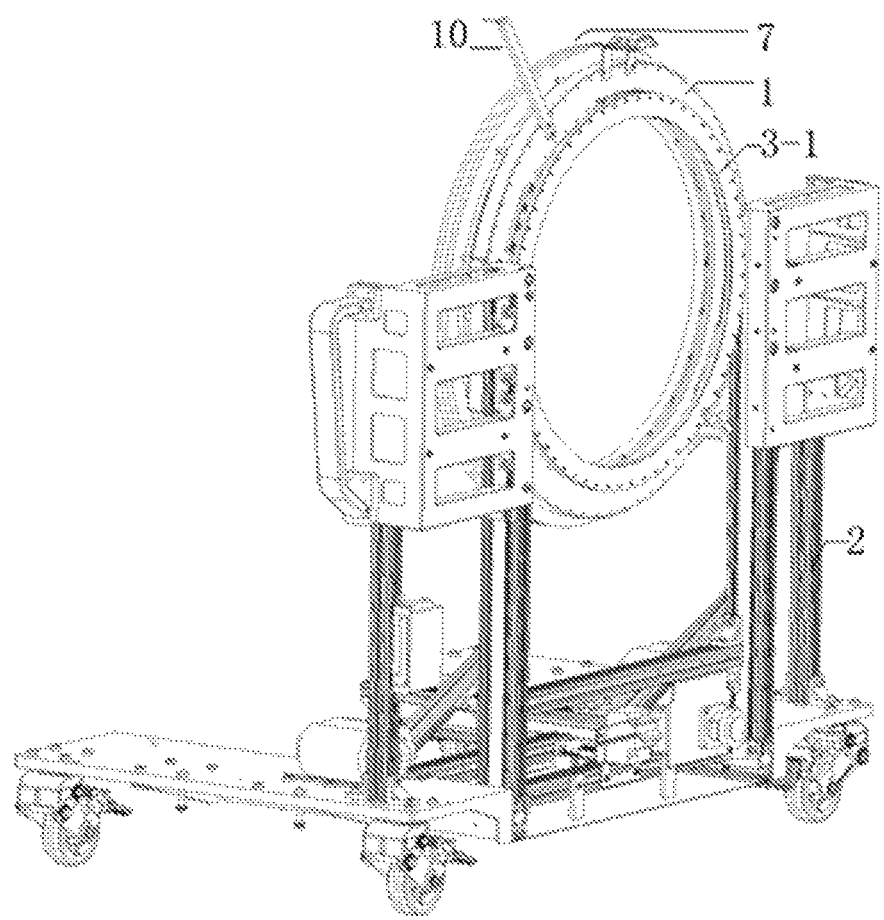
FIG. 1 is a diagram of the rack.
Figure 2:
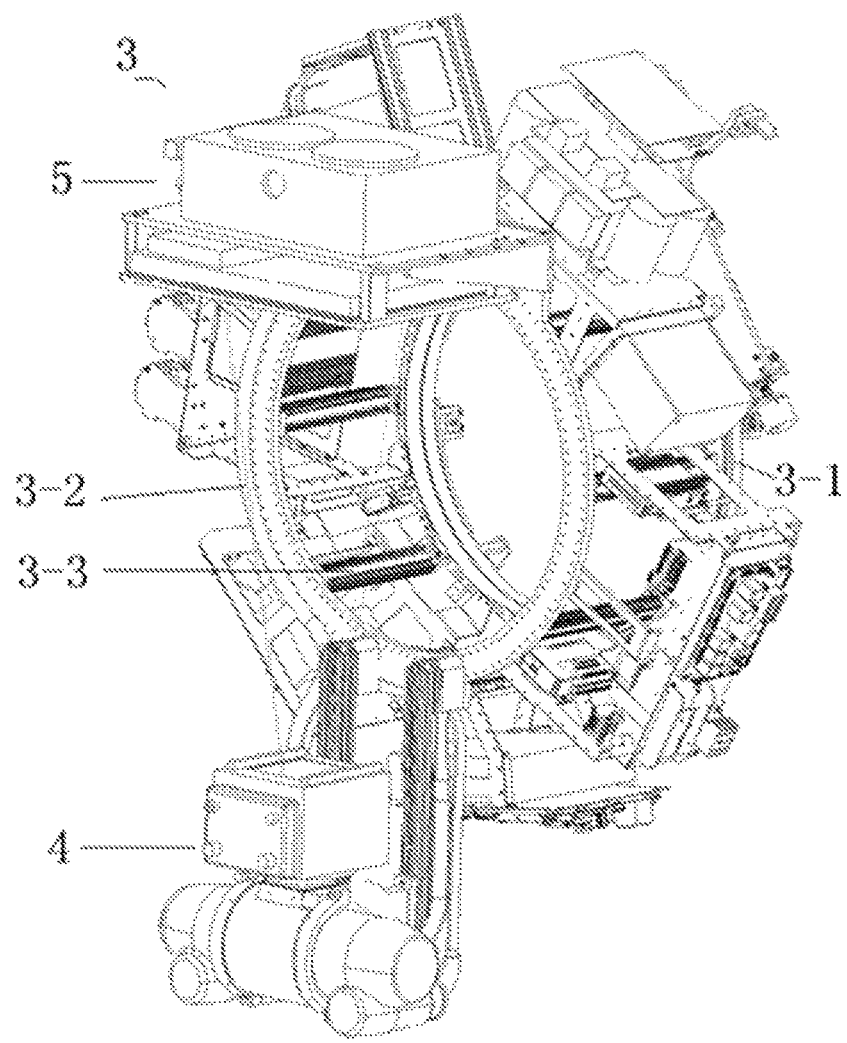
FIG. 2 is a rear side view of the cage-type rotating member.

As shown in FIGS. 1 and 2, the present invention provides a cage-type CT scanner for medical purposes, including:

A rack 1, vertically arranged on the mobile unit 2 of the CT scanner; a cage-type rotating member 3, including a first rotating accessory 3-1, a second rotating accessory 3-2, and a ridge 3-3 that connects the first rotating accessory 3-1 and the second rotating accessory 3-2; the first rotating accessory 3-1 is arranged on the rack 1 through the slewing bearing in a rotatable manner; the cage-type rotating member 3 and the rack 1 form a ring structure whose center serves as the scanning hole; an imaging system, equipped with the X-ray source assembly 4 and the detector assembly 5 that are arranged on the walls at the same side of the second rotating accessory 3-2, symmetrically along the shaft center; the X-ray source assembly 4 and the detector assembly 5 are fixed at the second rotating accessory 3-2; the detector assembly 5 receives the emergent rays from the X-ray source assembly 4; and a turbine assembly 6, arranged on the first rotating accessory 3-1 in a slanting direction; the gearwheel 7 engaged with the turbine assembly is fixed on the side of the rack 1 that is not the side where the first rotating accessory 3-1 is; the first rotating accessory 3-1, the rack 1, the gearwheel 7 and the second rotating accessory 3-2 have coincident axes; the turbine assembly 6, with the help of the motor 8, drives the cage-type rotating member 3 to rotate around the gearwheel 7; the cable, through the cage-type rotating member 3, connects the power source and the imaging system. The X-ray source assembly 4 emits cone beams, and the imaging system scans and images the object by completing dynamic volumetric scanning in one revolution.

In the solution above, the outer ring of the slewing bearing is installed on the inner ring of the rack 1; the first rotating accessory 3-1 has an outer ring that is smaller than the inner ring of the rack 1, and is subject to clearance fit with the rack 1 through the slewing bearing; a ball or roller is installed between the wall on the side where the outer ring of the first rotating accessory 3-1 protrudes and the rack 1; on the outer wall of the inner ring of the rack 1, a groove is arranged to house the ball or roller; the radius of the rack 1 is between the gearwheel 7 and the first rotating accessory 3-1, and the gearwheel 7 is a helical gear bolted on the rack 1.

Figure 3:
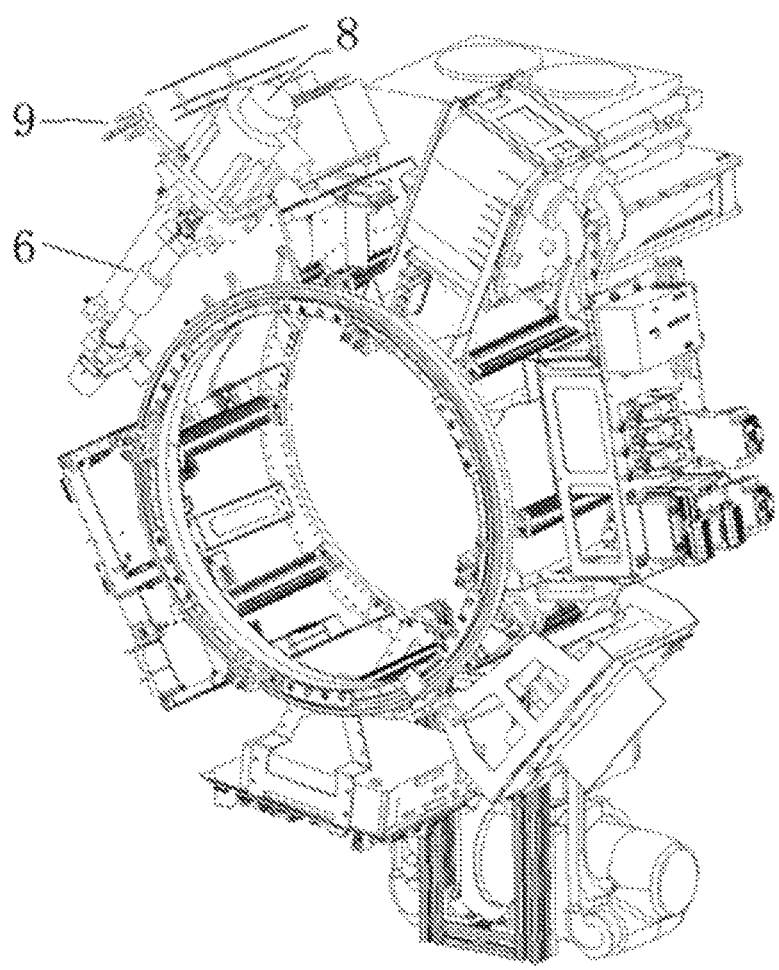
FIG. 3 is a front side view of the cage-type rotating member.
Figure 4:
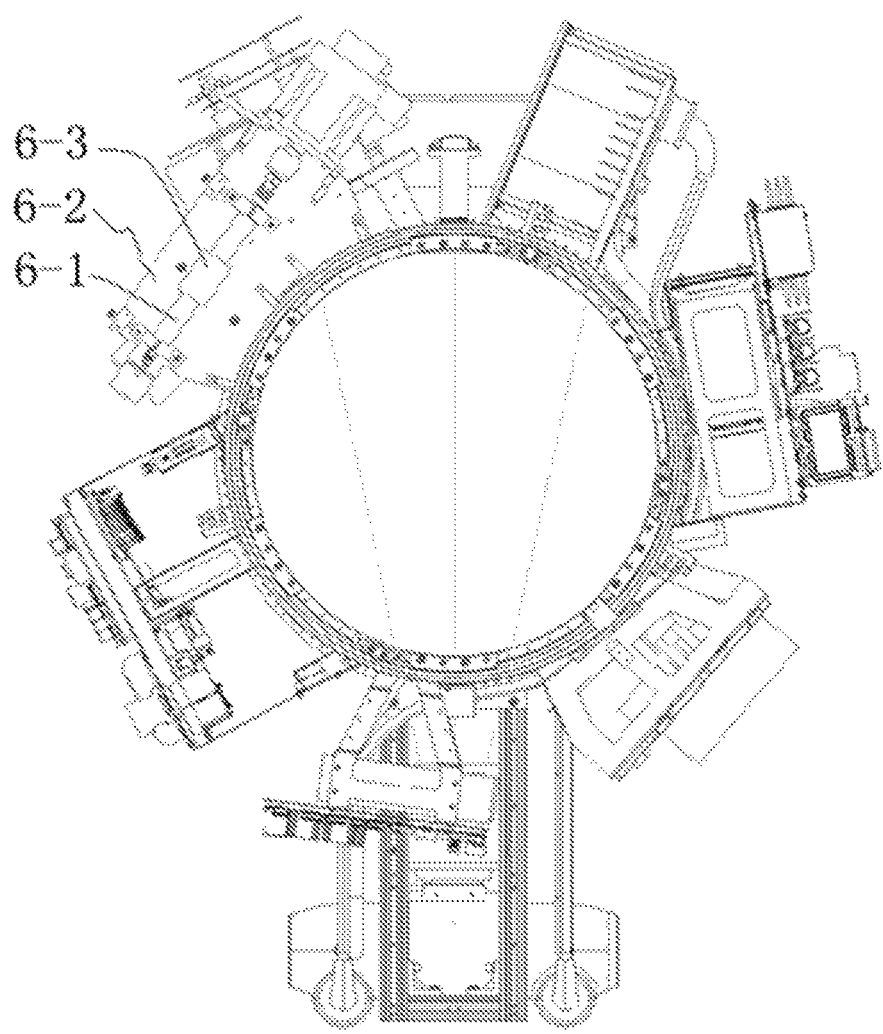
FIG. 4 is a front view of the cage-type rotating member.

As shown in FIGS. 3 and 4, the turbine assembly 6 includes: a turbine shaft 6-1, arranged on the cage-type rotating member 3 by means of a base plate 6-2; the base plate 6-2 is fixed on the ridge 3-3 of the cage-type rotating member 3 by means of a structural section; the turbine shaft 6-1 is supported by the base plate 6-2 with roller bearings on both sides; a worm 6-3, connected with the turbine shaft 6-1 by means of an internal spline; the turbine shaft 6-1 is connected with the engine by means of the brake device on one end and is provided with a belleville spring and gland on the other end; when applied with an axial force generated when the worm 6-3 and the gearwheel 7 are engaged to transfer force, the turbine shaft 6-1 directly drives the cage-type rotating member 3 to rotate around the shaft clockwise or counterclockwise depending on the rotation of the motor 8; a brake switch 9, equipped with a groove on one side; the groove is fitted with the protruding part of the initial bar 10, and on the other end, fixed on the base plate and close to the motor 8; when the motor 8 does not work, the protruding part of the initial bar 10 will be stuck in the groove of the brake switch, that is to say, the brake switch 9 is at the initial position.

Alternatively, an industrial personal computer A is installed on the cage-type rotating member 3 and under the detector assembly 5, and is equipped with a power source and a command processor. The detector assembly 5 includes an image pre-processing device which processes a first image signal. The first image signal has an imaging portion that shows the photographed object and a margin portion around the imaging portion. The image pre-processing device includes: a margin detecting member that detects the margin portion of the first image signal; a concerned area setting member that sets an initial concerned area corresponding to the imaging portion of the first image signal based on the margin portion detected by the margin detecting member; and a concerned area image generation member that generates a concerned area image signal which indicates the initial concerned area set by the concerned area setting member.

Alternatively, the concerned area image generation member includes: a cutting portion that cuts from the first image signal the initial concerned area set by the concerned area setting member; and a zooming member that generates an image as the concerned area image signal after it zooms in or out on the displayed object corresponding to the first image signal and after the cutting member cuts the initial concerned area from the first image signal.

Alternatively, the cage-type rotating member 3 is equipped with a display that includes an industrial personal computer B, an AC-DC power source and a graphic display. The industrial personal computer B is installed on the ridge at one side of the rotating member while the graphic display is installed in a movable manner on the ridge at the other side of the rotating member. The industrial personal computer B is powered by the AC-DC power source. The display shows images output by the image processing device.

Alternatively, a wireless data communication module is provided on the cage-type rotating member, including: a first memory, so constructed as to store clinical data; a transmitter, so constructed as to transmit the clinical data based on a first communication protocol; a receiver, so constructed as to receive augmented data based on a second communication protocol; and a second memory, so constructed as to store the augmented data. The augmented data are based on the clinical data.

Alternatively, an isolation transformer and an image processing computer are arranged under the mobile unit; the storage medium connected with the image processing computer is installed on the panel. The image processing computer pre-produces a 3D CT image reconstruction algorithm.

Alternatively, an emergency stop button switch and a ray indicator light are installed on the mobile unit.

The power supply is realized by a slip ring.

Alternatively, the design requirements and main technical indicators are given below:

1. Weight and dimensions of the whole machine.

The weight of the whole machine is controlled within 300 kg and its dimensions allow a nurse to move it in and out of ordinary wards in hospitals.

2. X-ray tube: Varian G1086.

Applicable tube shell: B-160H;

Installation position: rotating rack, so installed as to move toward a plurality of fixed positions along the detector direction;

The package dimensions of X-ray tubes and the dimensions of applicable tube shells are given in the product data in the website;

Dimensions of beam limiter in front of beam outlet of X-ray tube: 19 cm in length and 25 cm in width along the X-ray tube package direction (longest), and 19 cm in depth along the X-ray emission direction. See RF202 Instructions for Beam Limiter;

On the beam limiter, linear indicator lights (red or green laser) are installed on both sides of the position where beams are orthogonal, to adjust the angles of the indicator lights on the detector and at the intersection with the rotating center axis.

3. Detector: Varian Pax Scan 4030CB.

Weight: 16 kg; dimensions: 466 mm×366 mm×64 mm.

Applicable power source and command processor: 279.4 mm×258.75 mm×76.2 mm; 8.4 kg.

Installation position: rotating rack, installed under the detector together with the industrial personal computer A.

4. Power source: SHFR400-CBCT (bipolar power source, equipped with HV cables and standard connectors)

Installation position: rotating rack.

Dimensions and weights of 6 components of power source:

Hv transformer: 12.8 kg, 215.5×260×291.9 mm.

Main control board module: 1.2 kg, 331.5×230×41.5 mm.

Inverter module: 7 kg, 351.2×212×214.2 mm.

Starter module: 0.8 kg, 158×194.4×48 mm.

Input module: 6 kg, 135×215×43 mm.

Optimal interface board module: 0.3 kg, 150.7×27.3×112.7 mm.

Heat exchanger (c/w pump, oil inlet and outlet pipes).

Model: Varian HE-581; dimensions: 381(L)×304.8(W)×127(H) (the installation dimensions and structure are given in the product instructions); weight: 16.5 kg (or greater if oil pipes are provided); installation position: rotating rack.

6. Rotating member of the whole machine.

Rotating mode: the rotating member rotates freely, supported by two bearings or a single angular contact bearing, and the displacement of the rotating center due to shaking does not exceed 0.2 mm.

Transmission mode: gear+screw; the gear (external) is installed at the rotating rack, and the screw+coupling+motor are installed at the mobile rack Driving motor (Yaskawa, c/w rotary encoder): model: SGMGV-20ADE6S; dimensions and weight: as required; installation position: mobile rack.

Motor driver: model: SGDV-180A 01 A 000 000; dimensions and weight: as required; installation position: mobile rack.

Rotary encoder (Omron): model: E6C2-CWZ3E 600P/R2; dimensions and weight: as required; installation position: rotating rack, the gear (internal) is installed at the mobile rack, and the angle measurement gear+rotation position photoelectric encoder are installed at the rotating rack.

Industrial personal computer A: model: ARK-5260 (Advantech); dimensions: 137×189×221 mm.

Photoelectric sensor B (scanning starting position): model: E3Z-G62 2M (Omron), grooved-type, c/w built-in amplifier; installation position: the photoelectric sensor is installed on the rotating rack and the position stopper is installed on the mobile rack; it is necessary to remember this is a dual-optical-path photoelectric sensor; the alignment and positioning errors shall not exceed ±0.5 mm when the rotating rack is rotating.

AC-DC power source (for industrial personal computer A; 12VDC5A): installation position: rotating rack.

Dynamic balance: the weight difference shall not exceed 10%; and the displacement of the rotating center shall not exceed 0.2 mm.

Max. speed: 10 seconds/revolution.

Power supply mode: slip ring (three rings, each equipped with three sliding contact electrodes at least and bearing current above 16 A).

Passable diameter of center: over 500 mm.

7. Movement and fixing support of whole machine.

The whole machine may move freely on a horizontal plane when it is stopped, and when it is working, shall be fixed relative to the ground during the rotation of the tube and the detector. During the rotary scanning, the rack shall not move or shake, with the error controlled within ±0.5 mm.

A 350 W isolation transformer and a graphic processing computer (model to be determined) are arranged under the mobile rack; the storage medium interface with the graphic computer is installed on the outer panel.

8. Display.

Industrial personal computer B (c/w resistive touchscreen and computer): model: IPPC-8151S (15", Advantech); installation position: fixed on the right of the tube and detector side when the mobile rack faces the side of the central hole.

AC-DC power source (for industrial personal computer A; 12VDC5A): installation position: rotating rack.

Graphic display (c/w resistive touchscreen): model: FPM-7211 W (21", Advantech); installation position: installed in a movable manner on the left of the tube and detector side when the mobile rack faces the side of the central hole (may be observed from different positions).

9. Movement noise: not above 60 dB (measured at a distance of 1 m).

10. IR photoelectric data communication module: installation position: one on rotating and mobile racks respectively; two modules are aligned when the rotating rack stops positioning, with the error not exceeding ±1°.

11. Wireless data communication module: installation position: one on rotating and mobile racks respectively; two modules are aligned when the rotating rack stops positioning.

12. Photoelectric sensor A (scanning stopping position): model: E3Z-G62 2M (Omron), grooved-type c/w built-in amplifier; installation position: the photoelectric sensor is installed on the rotating rack and the position stopper is installed on the mobile rack; it is necessary to remember this is a dual-optical-path photoelectric sensor; the alignment and positioning errors shall not exceed ±0.5 mm when the rotating rack is rotating.

13. Emergency stop button switches and ray indicator lights are installed on the console and the mobile rack (housing), and the ray indicator lights may be observed from all positions in the room.

14. A patient's breath indicator light (not rotary) is installed above the central hole.

15. A 360° IR probe for receiving remote control signals is installed on the top of the mobile rack.

The present invention provides a cage-type CT scanner that avoids center instability, belt slippage and accuracy-degrading vibration faced by existing bedside CT scanners. Such cage-type CT scanner involves great design innovations that allow the maneuverability of the whole machine: a pulse-based exposure and imaging means is designed to reduce radiation dosages; a new imaging geometry is designed to enlarge the diameter of the scanning hole; the mechanical structure is optimized to reduce the weight and dimensions of the scanner; rapid dynamic volumetric scanning is adopted to increase applications of mobile CT scanners, even including field rescues.

The present invention involves rapid dynamic volumetric scanning and image reconstruction based on a new reconstruction algorithm.

As said above, the present invention provides an innovative imaging geometry to enlarge the diameter of the scanning hole.

While its embodiments are described above, the present invention may be used wherever applicable, in addition to the applications shown in the specification and embodiments. Those skilled in the art, upon attaining an understanding of the foregoing, may readily conceive of alterations to these embodiments. Therefore, the present invention is not to be limited to the details and drawings given herein, but is to be controlled by the limitations set forth in the claims and any equivalents thereof.

What is claimed is:

1. A cage-type CT scanner, which comprises:
a rack, vertically arranged on a mobile unit of the CT scanner;
a cage-type rotating member, including a first rotating accessory, a second rotating accessory, and a ridge that connects the first rotating accessory and the second rotating accessory; the first rotating accessory is so arranged on the rack through a slewing bearing in a rotatable manner; the cage-type rotating member and the rack form a ring structure whose center serves as a scanning hole;
an imaging system, equipped with an X-ray source assembly and a detector assembly that are arranged on the walls at the same side of the second rotating accessory, symmetrically along a shaft center; the X-ray source assembly and the detector assembly are fixed at the second rotating accessory; the detector assembly receives emergent rays from the X-ray source assembly;
and a turbine assembly, arranged on the first rotating accessory in a slanting direction; a gearwheel engaged with the turbine assembly is fixed on the side of the rack that is not the side where the first rotating accessory is; the first rotating accessory, rack, gearwheel and second rotating accessory have coincident axes; the turbine assembly, with the help of a motor, drives the cage-type rotating member to rotate around the gearwheel; a cable, through the cage-type rotating member, connects the power source and the imaging system.

2. The cage-type CT scanner of claim 1, wherein the X-ray source assembly emits cone beams, and the imaging system scans and images the object by completing dynamic volumetric scanning in one revolution, an outer ring of the slewing bearing is installed on an inner ring of the rack; the first rotating accessory has an outer ring that is smaller than the inner ring of the rack, and is subject to clearance fit with the rack by means of the slewing bearing; a ball or roller is installed between the wall on the side where the outer ring of the first rotating accessory protrudes and the rack, and on the outer wall of the inner ring of the rack, a groove is arranged to house the ball or roller.

3. The cage-type CT scanner of claim 1, wherein the radius of the rack is between the gearwheel and the first rotating accessory, and the gearwheel is a helical gear bolted on the rack; the turbine assembly includes:
a turbine shaft, arranged on the cage-type rotating member by means of a base plate; the base plate is fixed on the ridge of the cage-type rotating member by means of a structural section; the turbine shaft is supported by the base plate with roller bearings on both sides;
a worm, connected with the turbine shaft by means of an internal spline; the turbine is connected with an engine by means of the brake device on one end and is provided with a belleville spring and gland on the other end; when applied with an axial force generated when the worm and the gearwheel are engaged to transfer force, the turbine shaft directly drives the cage-type rotating member to rotate around the shaft clockwise or counterclockwise depending on the motor rotation;
a brake switch, equipped with a groove on one end; the groove is fitted with a protruding part of an initial bar, and on the other end, fixed on the base plate and close to the engine; when the motor does not work, the protruding part of the initial bar will be stuck in the groove of the brake switch to define the brake switch is at the initial position.

4. The cage-type CT scanner of claim 1, wherein an industrial personal computer A is installed on the cage-type rotating member and under the detector assembly, and is equipped with a power source and a command processor;
the detector assembly includes an image pre-processing device which processes a first image signal;
the first image signal has an imaging portion that shows a photographed object and a margin portion around the imaging portion;
the image pre-processing device includes: a margin detecting member that detects the margin portion of the first image signal; a concerned area setting member that sets an initial concerned area corresponding to the imaging portion of the first image signal based on the margin portion detected by the margin detecting member; and a concerned area image generation member that generates a concerned area image signal which indicates the initial concerned area set by the concerned area setting member.

5. The cage-type CT scanner of claim 4, wherein the concerned area image generation member includes: a cutting member that cuts from the first image signal the initial concerned area set by the concerned area setting member; and a zooming member that generates an image as the concerned area image signal after it zooms in or out on the displayed object corresponding to the first image signal and after the cutting member cuts the initial concerned area from the first image signal.

6. The cage-type CT scanner of claim 1, wherein the cage-type rotating member is equipped with a display that includes an industrial personal computer B, an AC-DC power source and a graphic display;
the industrial personal computer B is installed on the ridge at one side of the rotating member while the graphic display is installed in a movable manner on the ridge at the other side of the rotating member, and may be observed from different positions;
the industrial personal computer B is powered by the AC-DC power source;
the display shows images output by an image processing device.

7. The cage-type CT scanner of claim 1, wherein a wireless data communication module is provided on the cage-type rotating member, including:
a first memory, so constructed as to store clinical data;
a transmitter, so constructed as to transmit the clinical data based on a first communication protocol;
a receiver, so constructed as to receive augmented data based on a second communication protocol;
and a second memory, so constructed as to store the augmented data;
the augmented data are based on the clinical data.

8. The cage-type CT scanner of claim 1, wherein an emergency stop button switch and a ray indicator light are installed on the mobile unit; an isolation transformer and an image processing computer are arranged under the mobile unit; a storage medium connected with the image processing computer is installed on the panel;
the image processing computer pre-produces a 3D CT image reconstruction algorithm; a power supply is realized by a slip ring.

* * * * *